United States Patent [19]

Junnila

[11] Patent Number: 4,980,277

[45] Date of Patent: Dec. 25, 1990

[54] CRYOPROTECTANT SOLUTION AND METHOD

[75] Inventor: Matti A. J. Junnila, Helsinki, Finland

[73] Assignee: Cultor Ltd., Helsinki, Finland

[21] Appl. No.: 109,495

[22] Filed: Oct. 16, 1987

[51] Int. Cl.[5] .............................................. A01N 1/02
[52] U.S. Cl. ........................................... 435/2; 435/1; 435/240.1; 62/64
[58] Field of Search ........................... 435/2, 1; 62/64; 128/DIG. 27; 252/403

[56] References Cited

FOREIGN PATENT DOCUMENTS

| | | | |
|---|---|---|---|
| 609524 | 6/1978 | U.S.S.R. | 435/2 |
| 677750 | 8/1979 | U.S.S.R. | 435/2 |
| 888896 | 12/1981 | U.S.S.R. | 435/2 |

OTHER PUBLICATIONS

Chemical Abstracts, vol. 97 (No. 13), Abstract No. 108,676s, Oikawa.
Chemical Abstracts, vol. 89, No. 1, Abstract No. 4855t, Inoue.
Chemical Abstracts, vol. 71, (1969), Abstract No. 934y, Sakai.
Chemical Abstracts, vol. 71, (1969), Abstract No. 10471j, Sakai.
Brearly et al., *Optimal Concentrations for non-penetrating Cryopreservatives of Human Blood*, Sep. 14–17, 1987 (124th British Pharmaceutical Conference), Journal of Pharmaceutical Pharmacology 39 (Suppl.) 1987, p. 30.
Coughlan et al., *The Role of Glycinebetaine in the Protection of Spinach Thylakoids Against Freezing Stress* 1982, pp. 62–69.
Anchordoguy et al., *Modes of Interaction of Cryoprotectants with Membrane phospholipids during Freezing*, Jan. 15, 1987, Cryobiology pp. 324–331.
Higgins et al., *A Comparative Investigation of Glycinebetaine and Dimethylsulfoxide as Liposome Cryoprotectants* J. Phar. Pharmacol., 1987, 39: pp. 577–582.

*Primary Examiner*—Sam Rosen
*Attorney, Agent, or Firm*—Baker & McKenzie

[57] ABSTRACT

This invention relates to an improved cryoprotectant solution for viable cells, such as sperm, ova and blood cells which contains an effective amount of betaine.

6 Claims, No Drawings

CRYOPROTECTANT SOLUTION AND METHOD

I. FIELD OF THE INVENTION

This invention relates to an improved cryoprotectant solution for viable cells such as sperm, ova and blood cells. The solution comprises an aqueous suspending vehicle which is physiologically acceptable to the cells and which contains betaine. In a method aspect, the invention relates to an improved method for the cryopreservation of viable cells by maintaining the cells at a cryogenic temperature in an aqueous suspending vehicle which contains betaine.

II. BACKGROUND OF THE INVENTION

Freezing has long been used or contemplated to preserve living cells, such as sperm, ova and blood cells; frozen storage permits the use of such cells after they have been removed or separated from the original organism. Indeed, Mantegazza, in 1866, appears to have first proposed the use of frozen banks to preserve human sperm. (Mantagazza, D., Sullo sperma umano, Rendic. Reale., Inst. Lomb. 3:183 (1866)).

For example, fresh sperm taken from a male is viable for a relatively short period of time, e.g. between about one to eight days; it is often necessary and/or advantageous to utilize the sperm long after it has been collected, e.g. for several months. Similarly, female ova taken from the womb are viable for only a short period of time. Various methods, principally freezing, have been employed to preserve the sperm and/or ova for relatively long periods of time; the need to effectively store sperm and/or ova has grown along with the increase in artificial insemination. Freezing sperm or ova permits, for example, a domestic animal breeder (for cattle, horses, swine, goats, poultry and the like) to maintain stocks of valuable sperm and/or ova for use when necessary also enables the transport of said stocks for breeding purposes which is less expensive and troublesome than transporting livestock, and permits genetically superior males to inseminate larger number of females. Artificial insemination has also been used in the human context for various medical and health reasons.

The storage and preservation of living cells such as sperm, ova and red blood cells has, however, proved to be quite troublesome because the survivability of viable cells using prior art freezing methods is often quite low. Freezing conditions are relatively harsh and thermal shock or other phenomena such as crystal formation which results from both freezing and thawing conditions often kills the cells. Therefore, maximizing the viability of thawed cells has been the goal of many researchers. For example, in the context of sperm aliquots, a thawed preparation must exhibit certain minimum fertility, typically measured by the motility of the sperm cells, or it is unlikely that the aliquot could successfully be used for artificial insemination.

The prior art discloses various methods for improving the survivability of frozen cells such as sperm and ova. U.S. Pat. No. 4,007,087 (Ericsson) discloses a sperm fractionation and storage method which claims to increase the percentage of motile sperm which survive frozen storage. Ericsson discloses a method whereby motile sperm are separated from non-motile, defective or dead sperm; the fraction containing the motile sperm is then frozen. Ericsson reports that his method increases the fertility of a sperm sample by enhancing evironmental (the ratio of total sperm to motile sperm) and viability (progressiveness of motility of the motile sperm) factors affecting the fertility of a sample, but his method does not improve the population (motile sperm count) factor which is possibly the most critical.

U.S. Pat. No. 3,791,384 (Richter et al.) discloses a method for deep freezing and thawing boar sperm which includes inactivating the fresh sperm by means of an inactivating solution which includes dextrose, dihydrate of ethlenedinitrotetra-acetic acid, sodium citrate and sodium hydrogencarbonate. Richter reports that inactivation of the sperm gives them greater power of resistance to freezing.

U.S. Pat. Nos. 4,429,542 (Sakao et al.), 4,487,033 (Sakao et al.), 3,893,308 (Barkay et al.) and 4,480,682 (Kameta et al.) all disclose different freezing methods which claim to improve the fertility of sperm and ova samples. In all of these methods, the temperature of sperm and ova samples in solution is lowered by various means which attempt to reduce the thermal shock and increase the survivability of the viable sperm and ova present. Most of these methods are, however, complex, cumbersome and expensive to utilize. Other freezing methods are also used including the "Sherman" method of rapid freezing in liquid nitrogen vapors (Sherman, J. K., Improved Methods of Preservation of Human Spermatozoa by Freezing and Freeze Drying, Fertil. Steril., 14:49–64 (1963), and the "Behrman-Sanada" method of gradual freezing (Behrman et al. Meterologous and Humologus Inseminations with Human Semen Frozen and Stored in a Liquid Nitrogen Refrigerator., Fertil. Steril. 17:457–466 (1966)).

In most freezing processes, the living cells — prior to freezing — are diluted with a physiologically acceptable cryoprotectant solution. In 1949, it was discovered that glycerol could be successfully used as cryoprotectant agent for the freezing of bovine sperm (Polge et al. Revival of Spermatozoa After Vitrification and Dehydration at Low Temperatures, Nature 164:666 (1949)) and since that time, the standard cryoprotectant solutions has contained glycerol, egg yolk, a sodium citrate, a buffer system, glucose, glycerine and sometimes an antibiotic or antibiotics, for example the "Ackerman" solution: Behrman and Ackerman, *Am. J. Obstet. and Gynecol.*, 103:654–655 (1969). The effectiveness of the cryoprotectant diluent is critical to the survivability of the cells which, in the context of sperm or ova aliquots, relates directly to the fertility of the aliquot.

It has now been discovered that a cryoprotectant solution for viable cells which comprises an aqueous suspending vehicle which is physiologically acceptable to the cells and contains betaine significantly increases the survivability of the cells. For example, sperm samples frozen with the cryoprotectant solution of the present invention exhibit a dramatic increase in motility compared to samples frozen with typical cryoprotectants which do not contain betaine. The instant invention provides an effective, yet relatively simple and inexpensive cryoprotectant solution and method for freezing and preserving living cells.

III. SUMMARY OF THE INVENTION

The present invention contemplates a cryoprotectant solution for viable cells which enhances the survivability of such cells. The cryoprotectant solution comprises an aqueous suspending vehicle which is physiologically acceptable to the cells and contains betaine in an amount in the range of about 1% to about 30% by weight of said solution. Preferably, the concentration of betaine in the cryoprotectant is about 25% by weight of said solution or less. A specific cryoprotectant solution contains betaine, and additionally lactose, egg yolk, glycerol, glucose, ethylene diamine tetraacetic acid ("EDTA"), sodium bicarbonate, trisodium citrate-2-hydrate, distilled water and penicillin.

In a method aspect, the present invention contemplates an improved method for freezing viable cells which comprises maintaining the cells at a cryogenic temperature in an aqueous suspending vehicle which is physiologically acceptable to the cells and which contains betaine in an amount in the range of about 1% to about 30% by weight of the vehicle.

IV. DETAILED DESCRIPTION OF THE PREFERRED EMBODIMENT

A. General

Cryoprotectant solutions for viable cells increase the number of cells which survive the freezing and thawing of stored aliquots and, therefore, increase the efficacy and utility of these aliquots. In the context of frozen sperm and ova, cryoprotectant solutions allow frozen aliquots of such cells to be stored for longer periods of time without a drop in fertility. The present invention can be utilized for the freezing of viable cells from any source, including, but not limited to, blood cells, sperm from horses, cattle, swine, poultry, sheep, goats, fish or man, and ova (both fertilized and unfertilized) from these sources.

Surprisingly, the addition of betaine to a cryoprotectant solution has been shown to effect a dramatic increase in the survivability of frozen cells. Betaine (1-carboxy-N,N,N-trimethanaminium hydroxide) is an inner salt (or zwitterion) which contains anionic and cationic sites within the same molecule. Betaine is also known as a so-called "biogenic amine". Although betaine has been known to act as a cryoprotectant for artificial liposomes, it has not, heretofore, been utilized as part of a cryoprotectant solution for living cells such as sperm, ova or the like. The exact mechanism by which betaine increases the viability of frozen cells is unknown.

The addition of betaine to a typical cryoprotectant solution used for the freezing of sperm samples, resulted in samples which — after thawing — exhibited substantial increase — compared to samples frozen with the same cryoprotectant solution that did not contain betaine — in cell motility. The sperm samples tested were taken from a stallion, but improved viability after freezing with the cryoprotectant solution of the instant invention is attainable for sperm from other sources, e.g. cattle, swine, poultry, fish, human, and the like, as well as for other cells — such as ova (fertilized or unfertilized) and blood cells.

B. Experimental

Betaine was included in cryoprotectant solutions at 1%, 2%, 5%, 10%, 15%, 20%, 25% and 30% levels by weight of said solutions. Control samples did not contain betaine In addition to betaine, the solution, in all experimental studies was constituted by:
52 ml 11 (wt)% aqueous lactose solution
23 ml Merck solution
20 ml egg yolk
5 ml 87 (wt)% glycerol
The Merck solution consisted essentially of:
6 g glucose
0.37 g EDTA
0.12 g sodium bicarbonate
0.375 g trisodiumcitrate-2-hydrate
100 ml distilled water
50.0 IU (International Units) of penicillin The cryoprotectant solution was added to samples of horse sperm collected by the open method with the first three jets taken. Each sample was acclimatized for 20 minutes before packaging and dilution; the temperature of the samples was 32° C. Samples of acclimatized sperm (1 ml) were packed in Eppendorf-tubes with 100 ul of cryoprotectant solution. The resulting samples were frozen in Cell Freezer Model R204 (Planer Products Ltd., USA) according to three methods:

METHOD I: The samples were maintained at 32° C. for 10 minutes. The sample temperature was first decreased at a rate of 1° C. per minute down to −7° C. The samples were maintained at −7° C. for 10 minutes; the sample temperature then was again decreased at a rate of 0.3° C. per minute to −30.C., and then further decreased at a rate of 0.1° C. per minute to −33° C. The samples were thereafter stored in liquid nitrogen at −196° C.

METHOD II: The samples were maintained at 32° C. for 10 minutes. The sample temperature was then decreased at a rate of 3° C. per minute until the temperature reached −35° C. The samples were then stored in liquid nitrogen at −196° C.

METHOD III: The samples were maintained at 32° C. for 10 minutes. The sample temperature was decreased at a rate of 1° C. per minute until the sample temperature reached −7° C. The sample temperature of −7° C. was maintained for 10 minutes and then decreased at a rate of 3° C. per minute until the temperature reached −35° C. The samples were thereafter stored in liquid nitrogen at −196° C.

All samples were thawed by melting in a water bath at 45° C. for about 1 minute.

Two experimental phases were carried out. In the first phase, three different ejaculates from one stallion were taken. Samples from each ejaculate were frozen with a cryoprotectant solution containing various levels of betaine as indicated above as well as some cryoprotectant solution with betaine. The three freezing methods (I, II and III above) were utilized for each set of samples. In the second phase the sperm from five stallions was collected and frozen with a cryoprotectant solution with a fixed level of betaine (about 25% by weight of said solution). Three trials, each done according to one of the freezing methods (I, II and III above) were carried out.

The thawed samples were tested to determine the viability of the sperm cells present. The following motility measurements were made:
1. total motility (%) ("total mot."): motility of cells, i.e. percentage of sperm cells present showing motility
2. "vmot" (um/s): average speed of sperm cells
3. progressive motility (%) ("progr."): percentage of sperm cells showing progressive swimming movements
4. v-progressive (um/s) ("vprogr"): average progressive speed of sperm cells Measurements were made by using a Lazymot instrument (BGT Biotechnik GmbH) using software sold under the trademark "Motilie" available from BGT Biotechnik GmbH. Motility of each sample was detected by a He-Ne laser and the results calculated utilizing the aforementioned software.

TABLE I

Motility of Thawed Sperm Samples - Freezing Method I

| Betaine concentration % | total mot (%) | vmot (um/s) | progr (%) | vprogr (um/s) |
|---|---|---|---|---|
| (0:control) | 8 | 28 | 7 | 54 |
| 1 | 11 | 30 | 10 | 58 |
| 2 | 10 | 30 | 9 | 59 |
| 5 | 9 | 27 | 7 | 57 |
| 10 | 15 | 31 | 11 | 62 |
| 15 | 30 | 39 | 19 | 75 |
| 20 | 67 | 44 | 35 | 77 |
| 25 | 83 | 51 | 48 | 78 |
| 30 | 64 | 52 | 41 | 82 |

TABLE II

Motility of Thawed Sperm Samples - Freezing Method II

| Betaine concentration % | total mot (%) | vmot (um/s) | progr (%) | vprogr (um/s) |
|---|---|---|---|---|
| (0:control) | 60 | 47 | 34 | 78 |
| 1 | 72 | 51 | 45 | 79 |
| 2 | 74 | 51 | 45 | 78 |
| 5 | 63 | 47 | 36 | 78 |
| 10 | 63 | 47 | 32 | 79 |
| 15 | 63 | 44 | 29 | 78 |
| 20 | 62 | 43 | 32 | 76 |
| 25 | 68 | 42 | 30 | 75 |
| 30 | 61 | 42 | 27 | 77 |

TABLE III

Motility of Thawed Sperm Samples - Freezing Method III

| Betaine concentration % | total mot (%) | vmot (um/s) | progr (%) | vprogr (um/s) |
|---|---|---|---|---|
| (0:control) | 20 | 32 | 13 | 60 |
| 1 | 45 | 41 | 24 | 73 |
| 2 | 21 | 30 | 11 | 65 |
| 5 | 51 | 39 | 30 | 71 |
| 10 | 58 | 42 | 26 | 78 |
| 15 | 63 | 45 | 32 | 78 |
| 20 | 77 | 48 | 38 | 78 |
| 25 | 76 | 50 | 47 | 78 |
| 30 | 73 | 51 | 49 | 80 |

Tables I, II and II set forth data from frozen sperm taken from a single stallion using freezing Methods I, II and III, respectively. In each case, samples frozen in a cryoprotectant solution containing betaine showed a greater total motility than the control sample frozen in a cryoprotectant solution which did not contain betaine. The samples frozen with a betaine containing cryoprotectant also showed increased vmot, progressive motility and velocity — progressiveness compared to the control samples further evidencing an increased viability of the cells. The optimal betaine concentration was in the range of about 20% to about 25% (by weight) of said solution. Significantly, the thawed samples, particularly within the optimum range, exhibited a high level of motility as measured by the various parameters, compared to that of fresh sperm samples (which generally exhibit, for example, total motility of about 60% to about 80%). The thawed samples using the cryoprotectant of the present invention will be highly suitable for use in artificial insemination procedures.

TABLE IV

MOTILITY OF THAWED SPERM SAMPLES FROM FIVE STALLIONS - FREEZING METHOD I

| Stallion | control solution (no betaine added) | | | | solution with 25% betaine added (by weight of solution) | | | |
|---|---|---|---|---|---|---|---|---|
| | mot (%) | vmot (u/s) | progr (%) | vprogr (um/s) | mot (%) | vmot (u/s) | progr (%) | vprogr (u/s) |
| Je | 51 | 41 | 23 | 77 | 66 | 44 | 33 | 77 |
| Ku | 45 | 38 | 21 | 73 | 66 | 41 | 27 | 77 |
| Lo | 13 | 30 | 10 | 62 | 87 | 61 | 57 | 85 |
| Ni | 48 | 43 | 25 | 79 | 70 | 44 | 35 | 75 |
| Ny | 41 | 36 | 18 | 73 | 72 | 45 | 26 | 76 |

TABLE V

MOTILITY OF THAWED SPERM SAMPLES FROM FIVE STALLIONS - FREEZING METHOD II

| Stallion | control solution (no betaine added) | | | | solution with 25% betaine added (by weight of solution) | | | |
|---|---|---|---|---|---|---|---|---|
| | mot (%) | vmot (u/s) | progr (%) | vprogr (um/s) | mot (%) | vmot (u/s) | progr (%) | vprogr (u/s) |
| Je | 8 | 28 | 8 | 58 | 65 | 44 | 31 | 77 |
| Ku | 11 | 29 | 9 | 59 | 58 | 43 | 28 | 79 |
| Lo | 47 | 42 | 25 | 79 | 80 | 53 | 46 | 80 |
| Ni | — | — | — | — | 12 | 30 | 10 | 61 |
| Ny | 13 | 30 | 10 | 63 | 65 | 46 | 37 | 78 |

TABLE VI

MOTILITY OF THAWED SPERM SAMPLES FROM FIVE STALLIONS - FREEZING METHOD III

| Stallion | control solution (no betaine added) | | | | solution with 25% betaine added (by weight of solution) | | | |
|---|---|---|---|---|---|---|---|---|
| | mot (%) | vmot (u/s) | progr (%) | vprogr (um/s) | mot (%) | vmot (u/s) | progr (%) | vprogr (u/s) |
| Je | 24 | 33 | 14 | 69 | 78 | 48 | 40 | 78 |
| Ku | 51 | 36 | 20 | 75 | 69 | 46 | 34 | 78 |
| Lo | 51 | 43 | 25 | 79 | 68 | 49 | 36 | 80 |
| Ni | 18 | 32 | 13 | 66 | 70 | 46 | 34 | 79 |
| Ny | 29 | 33 | 14 | 68 | 63 | 46 | 33 | 79 |

Tables IV, V and VI set forth data with respect to frozen sperm samples taken from five different stallions. Total motility and other motility parameters were measured for thawed samples which had been frozen with a cryoprotectant solution containing 25% betaine (by weight of said solution) and for thawed samples which had been frozen with a cryoprotectant soltuion that did not contain betaine. The data shows that the samples frozen with the cryoprotectant solution containing betaine exhibit a dramatic increase in total motility as well as the other motility parameters compared to the control samples; the samples frozen with the cryoprotectant solution of the present invention exhibit a high degree of viability after thawing. The total motility of the control samples was, in most cases, rather low which means that they would be poor choices for artificial insemination. On the other hand, the samples frozen with the cryoprotectant solution of the present invention exhibited a high degree of motility which make them excellent choices for artificial insemination.

The foregoing general discussion and experimental examples are intended to be illustrative of the present invention, and are not to be considered as limiting. Other variations within the spirit and scope of this invention are possible and will present themselves to those skilled in the art.

We claim:

1. A cryoprotectant solution for viable cells which comprises an aqueous suspending vehicle which is physiologically acceptable to the cells and contains cryoprotectant additives and betaine in an amount of about 25% by weight of said solution.

2. The cryoprotectant solution of claim 1 formulated for sperm cells.

3. A cryoprotectant solution for viable cells which is physiologically acceptable to the cells which comprises betaine in an amount of about 25% by weight of said solution and additionally contains lactose, egg yolk, glycerol, glucose, ethylene diamine tetracetic acid, sodium bicarbonate, trisodium citrate-2-hydrate, distilled water and penicillin.

4. A method for cryopreservation of viable cells which comprises the steps of maintaining the cells at a cryogenic temperature in an aqueous suspending vehicle which is physiologically acceptable to the cells, said vehicle containing betaine in an amount of about 25% by weight.

5. The method as claimed in claim 4 wherein said viable cells are sperm.

6. The method as claimed in claim 5 wherein said sperm are stallion sperm.

* * * * *